United States Patent [19]

Schläpfer-Illi, deceased

[11] 4,138,552
[45] Feb. 6, 1979

[54] 4-(V-TRIAZOLYL)-STYRYL OPTICAL BRIGHTENERS

[75] Inventor: Hans Schläpfer-Illi, deceased, late of Basel, Switzerland, by Nelly Schläpfer-Illi, Legal Representative

[73] Assignee: Ciba-Geigy Corporation, Ardsley, N.Y.

[21] Appl. No.: 777,981

[22] Filed: Mar. 16, 1977

[30] Foreign Application Priority Data

Mar. 26, 1976 [CH] Switzerland ............. 3815/76

[51] Int. Cl.$^2$ ............. C09K 11/06; C07D 249/06
[52] U.S. Cl. ............. 542/462; 252/301.24; 542/456
[58] Field of Search ............. 542/456, 462; 252/301.24, 301.28

[56] References Cited

U.S. PATENT DOCUMENTS

| 2,901,476 | 8/1959 | Gold et al. ............. 542/462 X |
| 3,459,744 | 8/1969 | Dorlaro et al. ............. 542/462 |
| 3,470,167 | 9/1969 | Sarker ............. 542/456 |
| 3,635,959 | 1/1972 | di Giovanod et al. ............. 542/456 |
| 3,759,900 | 9/1973 | Horstmann ............. 542/462 X |
| 4,014,871 | 3/1977 | Kormäny et al. ............. 542/462 |
| 4,022,772 | 5/1977 | Kormäny et al. ............. 542/462 |
| 4,032,503 | 6/1977 | Kormäny et al. ............. 542/456 X |
| 4,061,860 | 12/1977 | Kormäny et al. ............. 542/462 |

FOREIGN PATENT DOCUMENTS 1448  1/1969 Japan ............. 252/301.24
110/66 9/1967 Switzerland.

OTHER PUBLICATIONS

Kormany et al., CA 84: 181616h, 181617j, 181618k (1976), (effective date 03/04/1976).
Dorlars et al., CA 76:128834m (1972).

Primary Examiner—Thomas A. Waltz
Attorney, Agent, or Firm—Edward McC. Roberts; Prabodh I. Almaula

[57] ABSTRACT

Novel 4-(v-triazolyl)-styryl compounds of the formula

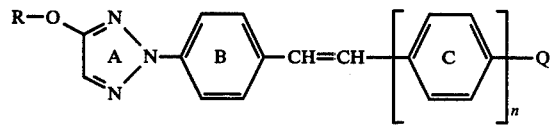

wherein n is 0, 1 or 2, R represents a hydrogen atom or an unsubstituted or substituted alkyl, alkenyl, aralkyl, alkanoyl or aroyl group and Q represents an unsubstituted or substituted 5-membered heterocyclic ring or, if n is 1 or 2, also represents hydrogen, the rings A, B and C being optionally substituted with further non-chromophoric substituents, processes for their preparation as well as a process for optically brightening organic materials on using said compounds are disclosed.

7 Claims, No Drawings

4-(V-TRIAZOLYL)-STYRYL OTPICAL BRIGHTENERS

The present invention relates to novel 4-(v-triazolyl)styryl compounds, a process for their manufacture and the use thereof as fluorescent brighteners for organic material.

The novel 4-(v-triazolyl)-styryl compounds have the formula

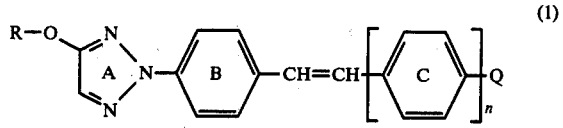

(1)

wherein n is 0, 1 or 2,

R represents a hydrogen atom or an unsubstituted or substituted alkyl, alkenyl, aralkyl, alkanoyl or aroyl group, and Q represents a 5-membered heterocyclic ring which is unsubstituted or substituted by non-chromophoric groups, and, if n is 1 or 2, also represents a hydrogen atom, whilst the ring A can contain one additional non-chromophoric substituent and the rings B and C can contain still further non-chromophoric substituents.

Suitable groups referred to in the definition of R are in particular:alkyl groups of 1 to 12, preferably of 1 to 4, carbon atoms, which can be substituted by alkoxy groups of 1 to 4 carbon atoms, carbalkoxy groups containing a total of 2 to 5 carbon atoms or hydroxyl, carboxyl, cyano or sulpho groups; alkenyl groups of 3 to 5, preferably 3, carbon atoms; aralkyl groups, preferably benzyl groups, which can be substituted in the phenyl nucleus by lower alkyl or lower alkoxy groups or by halogen atoms; alkanoyl groups containing a total of 2 to 12 carbon atoms which can be substituted by halogen atoms, lower alkoxy, carboxyl, carbalkoxy, cyano or hydroxyl groups; and aroyl groups, preferably monocyclic groups, in particular the benzoyl group, which can be substituted in the nucleus by lower alkyl or lower alkoxy groups or halogen atoms. Carbalkoxy groups preferably contain a total of 2 to 6 carbon atoms.

By non-chromophoric substituents of 5-membered heterocyclic rings Q and the rings A, B and C are meant for example: alkyl groups of 1 to 12 carbon atoms, cyclohexyl groups, phenylalkyl groups containing 1 to 3 carbon atoms in the alkyl moiety, phenyl which is unsubstituted or substituted by 1 or 2 members selected from the group consisting of chlorine, methyl or methoxy; alkoxy groups of 1 to 4 carbon atoms; phenoxy which is unsubstituted or substituted by 1 or 2 members selected from the group consisting of chlorine, methyl or methoxy; chlorine, fluorine or bromine atoms; cyano groups; —COOY, wherein Y represents a hydrogen atom, a salt-forming cation, an alkyl group of 1 to 5 carbon atoms or a benzyl group; CONY' ($Y_1'$), wherein Y' represents a hydrogen atom, an alkyl group of 1 to 6 carbon atoms, a hydroxyalkyl group of 1 to 4 carbon atoms, alkoxyalkyl of 2 to 8 carbon atoms, a phenyl or benzyl group and $Y_1'$ represents a hydrogen atom, an alkyl group of 1 to 6 carbon atoms, a hydroxyalkyl group of 1 to 4 carbon atoms or an alkoxyalkyl group of 2 to 8 carbon atoms, or Y' and $Y_1'$ together with the nitrogen atom to which they are attached represent a morpholino or piperidino radical; —SO₂OY, wherein Y is as defined above, —SO₂NY'($Y_1'$) wherein Y' and $Y_1'$ are as defined above; $C_1$-$C_6$-alkylsulphonyl, benzylsulphonyl or phenylsulphonyl which is unsubstituted or substituted by chlorine or methyl; or, if two substituents in the ortho-position are present, also $C_3$-$C_4$-alkylene or 1,3-butadienylene.

By 5-membered heterocyclic rings are meant preferably those containing oxygen and/or nitrogen atoms as ring members and which can contain in addition fused aromatic rings.

Compounds within the scope of the 4-(v-triazolyl)styryl compounds of the formula (1) to be singled out for special mention are:

(A) 4-(v-triazolyl)-styryl compounds of the formula

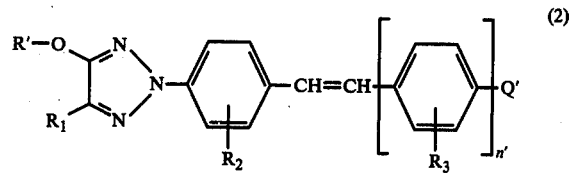

(2)

wherein n' is 1 or 2,

R' represents hydrogen, alkyl of 1 to 12 carbon atoms which is unsubstituted or substituted by alkoxy, hydroxyl, carboxyl, carbalkoxy or cyano, alkenyl of 3 to 5 carbon atoms, unsubstituted or substituted aralkyl, aroyl or alkanoyl of 2 to 12 carbon atoms, $R_1$ represents hydrogen, halogen, alkoxy of 1 to 12 carbon atoms, aryl, alkyl of 1 to 12 carbon atoms or the group —CH₂—Z, wherein Z represents hydroxyl, benzyloxy, or benzyloxy which is substituted by alkyl or alkoxy of 1 to 4 carbon atoms or by halogen, alkanoyloxy of 1 to 4 carbon atoms, alkoxy or alkylmercapto of 1 to 4 carbon atoms, a dialkylamino group containing 1 to 4 carbon atoms in each alkyl moiety, morpholino, piperidino or methyl-substituted morpholino or piperidino, or dialkylphosphono containing 1 to 4 carbon atoms in each alkyl moiety, each of $R_2$ and $R_3$ independently represents hydrogen, halogen, cyano, alkoxy of 1 to 4 carbon atoms or sulpho, and Q' represents hydrogen, halogen, alkoxy of 1 to 4 carbon atoms, carboxyl, carbalkoxy containing 1 to 4 carbon atoms in the alkoxy moiety, cyano, a benzoxazol-2-yl, 2-aryl-1,3,4-oxdiazol-5-yl or 3(5)-aryl-1,2,4-oxdiazol-5(3)-yl group which is unsubstituted or substituted by non-chromophoric groups, or represents the radical of the formula (3)  (4)

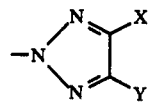 or 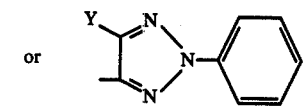

wherein the phenyl radical can be substituted by non-chromophoric groups, and

X represents the radical —O—R', wherein R' is as defined above, hydrogen, alkyl of 1 to 4 carbon atoms, aryl, styryl, aralkyl containing 1 to 4 carbon atoms in the alkyl moiety, halogen, or together with Y completes a 5- or 6-membered ring, and Y represents the above defined radical $R_1$, styryl, aralkyl containing 1 to 4 carbon atoms in the alkyl moiety, halogen, or together with X completes a 5- or 6-membered alicyclic ring,
whilst R₁ preferably represents hydrogen, chlorine or cyano; and (B) 4-(v-triazolyl)-styryl compounds of the formula

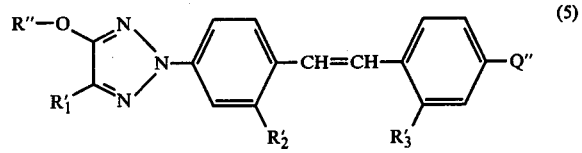

(5)

wherein

R″ represents alkyl of 1 to 12 carbon atoms which is unsubstituted or substituted by alkoxy, hydroxyl, carboxyl, carbalkoxy or cyano, alkenyl of 3 to 5 carbon atoms or unsubstituted or substituted benzyl, R₁′ represents hydrogen, chlorine, bromine, or the group —CH₂—Z, wherein Z represents hydroxyl, benzyloxy, benzyloxy which is substituted by alkyl or alkoxy of 1 to 4 carbon atoms or by halogen, alkanoyloxy of 1 to 4 carbon atoms, alkoxy or alkylmercapto of 1 to 4 carbon atoms, a dialkylamino group containing 1 to 4 carbon atoms in each alkyl moiety, morpholino, piperidino, methyl-substituted morpholino or piperidino, or dialkylphosphono which contains 1 to 4 carbon atoms in each alkyl moiety, each of R₂′ and R₃′ independently represents hydrogen, chlorine or cyano, and Q″ represents a benzoxazol-2-yl, 2-aryl-1,3,4-oxdiazol-5-yl or 3(5)-aryl-1,2,4-oxdiazol-5(3)-yl group which is unsubstituted or substituted by non-chromophoric groups.

In compounds of the formula (2), wherein Q′ is a radical of the formula (3), sulpho groups R₂ and R₃ are preferably in the ortho-position to the ethylene bridge.

Aryl as substituent of an oxdiazolyl group is to be understood as meaning phenyl, diphenyl and naphthyl groups which can contain substituents such as sulpho, alkyl or alkoxy groups or halogen atoms.

Preferred 4-(v-triazolyl)-styryl compounds are those of the formula

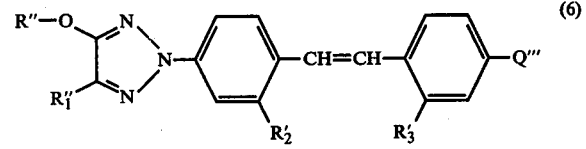

(6)

wherein

R″ represents alkyl of 1 to 12 carbon atoms which is unsubstituted or substituted by alkoxy, hydroxyl, carboxyl, carbalkoxy or cyano, alkenyl of 3 to 5 carbon atoms or unsubstituted or substituted benzyl, R₂″ represents hydrogen, chlorine or the group —CH₂—Z′, wherein Z′ represents hydroxyl, benzyloxy, alkanoyloxy of 1 to 4 carbon atoms or alkoxy of 1 to 4 carbon atoms, each of R₂′ and R₃′ independently represents hydrogen, chlorine or cyano, and Q‴ represents a radical of the formula

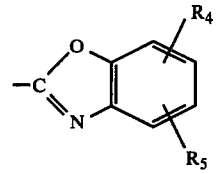

(7)

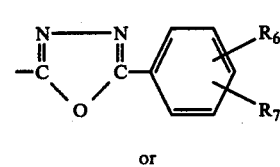

(8)

or

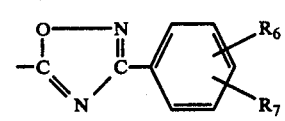

(9)

wherein

R₄ represents hydrogen or alkyl of 1 to 4 carbon atoms,

R₅ represents hydrogen, chlorine, alkyl of 1 to 4 carbon atoms, alkoxy of 1 to 4 carbon atoms, alkylsulphonyl of 1 to 4 carbon atoms, phenyl, phenylalkyl containing 1 to 4 carbon atoms in the alkyl moiety, cyclohexyl, carboxyl, carbalkoxy containing 1 to 4 carbon atoms in the alkoxy moiety or phenylsulphonyl, R₆ represents hydrogen, alkyl of 1 to 4 carbon atoms, alkoxy of 1 to 4 carbon atoms, chlorine, phenyl, phenylalkyl containing 1 to 4 carbon atoms in the alkyl moiety, or together with R₇ completes a fused benzene ring, R₇ represents hydrogen, alkyl of 1 to 4 carbon atoms, alkoxy of 1 to 4 carbon atoms, or together with R₆ completes a fused benzene ring.

The most preferred 4-(v-triazolyl)-styryl compounds are those of the formula

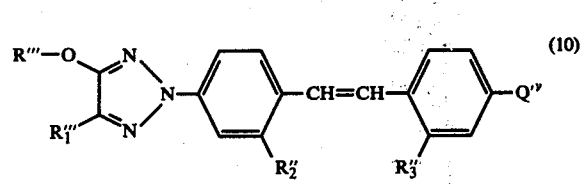

(10)

wherein

R‴ represents alkyl of 1 to 4 carbon atoms, allyl or benzyl,

R₁‴ represents hydrogen or chlorine, each of

R₂″ and R₃″ independently represents hydrogen or chlorine, and

Q^IV represents a radical of the formula

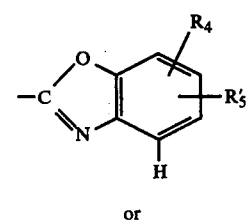

(11)

or

-continued

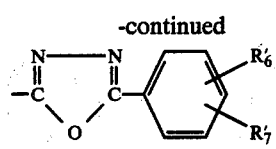

wherein
R₄ represents hydrogen or alkyl of 1 to 4 carbon atoms,
R₅' represents hydrogen, chlorine, alkyl of 1 to 4 carbon atoms, alkylsulphonyl of 1 to 4 carbon atoms or carbalkoxy which contains 1 to 4 carbon atoms in the alkoxy moiety,
R₆' represents hydrogen, alkyl of 1 to 4 carbon atoms, alkoxy of 1 to 4 carbon atoms, chlorine, phenyl, or together with R₇' completes a fused benzene ring, and
R₇' represents hydrogen or together with R₆' completes a fused benzene ring;
those of the formula

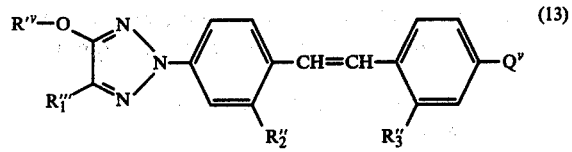

wherein
R'ᵛ represents alkyl of 1 to 4 carbon atoms or benzyl,
R₁''' represents hydrogen or chlorine,
each of
R₂'' and R₃'' independently represents hydrogen or chlorine, and
Qᵛ represents a radical of the formula

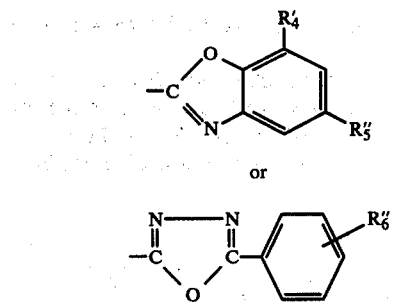

wherein
each of R₄' and R₅'' independently represents hydrogen or methyl and
R₆'' represents hydrogen, chlorine, methyl or methoxy; and those compounds of the formula

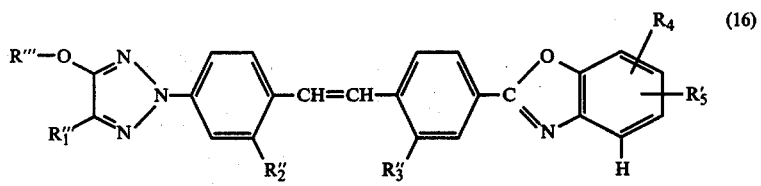

wherein
R'''' represents alkyl of 1 to 4 carbon atoms, allyl or benzyl,
R₁'''' represents hydrogen or chlorine,
each of
R₂'' and R₃'' independently represents hydrogen or chlorine,
R₄ represents hydrogen or alkyl of 1 to 4 carbon atoms and
R₅' represents hydrogen, chlorine, alkyl of 1 to 4 carbon atoms, alkylsulphonyl of 1 to 4 carbon atoms or carbalkoxy containing 1 to 4 carbon atoms in the alkoxy moiety.

The 4-(v-triazolyl)-styryl compounds of the formula (1) can be obtained in a manner known per se, for example by reacting a v-triazolyl-phenyl compound of the formula

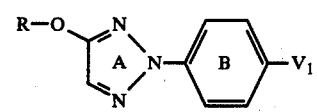

with a compound of the formula

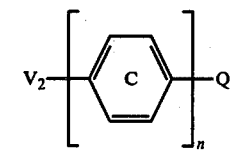

wherein R, O, n, A, B and C are as defined hereinbefore and one of the symbols V₁ and V₂ represents a —CHO group and the other represents a group of the formula

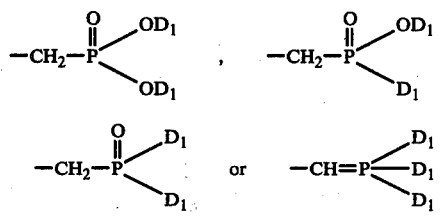

wherein D₁ represents an unsubstituted or substituted alkyl group, an aryl group, a cycloalkyl group or an aralkyl group.

This process of manufacture is advantageously carried out in inert solvents. Examples of such solvents in this connection are hydrocarbons, such as toluene and xylene or alcohols, such as methanol, ethanol, isopropanol, butanol, glycols, glycol ethers, such as 2-methoxyethanol, hexanols, cyclohexanol and cyclooctanol, and also ethers, such as diisopropyl ether, tetrahydrofuran and dioxan as well as dimethyl sulphoxide, dimethyl formamide and N-methylpyrrolidone. Polar organic solvents, such as dimethyl formamide and dimethyl sulphoxide, are particularly preferred. A number of the reactions can also be carried out in aqueous solution.

The temperature at which the reaction is carried out can vary within wide limits. It is determined by (α) the resistance of the solvent employed to the reactants, especially to the strong basic alkali compounds, (β) the reactivity of the condensation partners, and (γ) the strength of the combination of solvent and base as condensation agent.

In practice, temperatures between about 10° C. and 100° C. are possible as a rule, especially if either dimethyl formamide or dimethyl sulphoxide is used as solvent. The preferred temperature range is between 20° C. and 60° C.

Suitable strong basic alkali compounds are chiefly the hydroxides, amides and alcoholates (preferably those of primary alcohols containing 1 to 4 carbon atoms) of alkali metals; for reasons of economy, those of lithium, sodium and potassium are of primary interest. However, in principle and in special cases it is also possible to use with success alkali sulphides and carbonates, arylalkali compounds, e.g. phenyl-lithium or strong basic amines (including ammonium bases, e.g. trialkylammonium hydroxides).

4-(v-Triazolyl)-styryl compounds of the formula

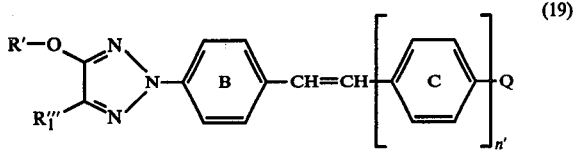

(19)

wherein the rings B and C can contain still further non-chromophoric substituents, n' is 1 or 2, Q represents a 5-membered heterocyclic ring which is unsubstituted or substituted by non-chromophoric groups or represents hydrogen, R' represents hydrogen, alkyl of 1 to 12 carbon atoms which is unsubstituted or substituted by alkoxy, hydroxyl, carboxyl, carbalkoxy or cyano, alkenyl of 3 to 5 carbon atoms, unsubstituted or substituted aralkyl, aroyl or alkanoyl of 2 to 12 carbon atoms, and $R_1'''$ represents hydrogen or chlorine, can also be obtained by diazotising a styryl compound of the formula

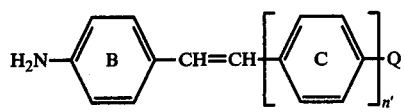

(20)

wherein n', Q, B and C are as defined above, and coupling the resultant diazo compound with α-nitroacetaldoxime to give a compound of the formula

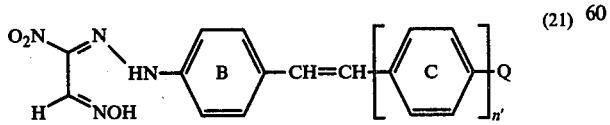

(21)

wherein n', Q, B and C are as defined above, and cyclising this compound in acid medium to give a compound of the formula (22)

wherein n', Q, B and C are as defined above, and reacting the resultant compound in a manner known per se to give a compound of the formula (19).

4-(v-Triazolyl)-styryl compounds of the formula (23)

wherein $R'^v$ represents alkyl of 1 to 12 carbon atoms or benzyl which is unsubstituted or substituted by chlorine or methyl, $R_1'''$ represents hydrogen or chlorine, and $Q^{v'}$ represents the radical wherein $R_4$ represents hydrogen or alkyl of 1 to 4 carbon atoms and $R_5'$ represents hydrogen, chlorine, alkyl of 1 to 4 carbon atoms, alkylsulphonyl of 1 to 4 carbon atoms or carbalkoxy containing 1 to 4 carbon atoms in the alkoxy moiety, can also be obtained by reacting a Schiff's base of the formula (24)

wherein $R'^v$ and $R_1'''$ are as defined hereinbefore and h represents hydrogen or chlorine, in a polar, neutral to basic organic solvent and in the presence of a strongly basic alkali compound, with a methyl compound of the formula (25)

(25a)

wherein $R_4$ and $R_5'$ are as defined above.

Compounds of the formula (23) can also be obtained by reacting a methyl compound of the formula

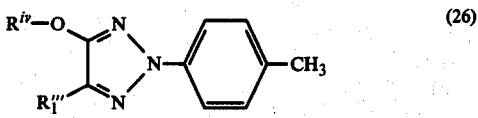

with a Schiff's base of the formula

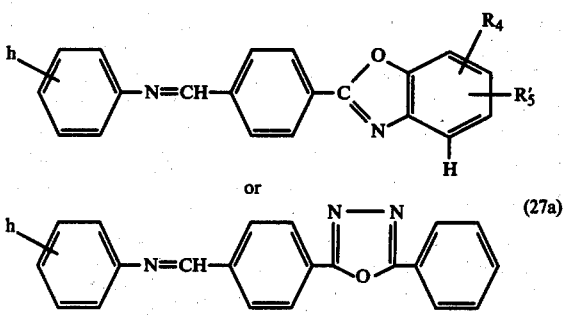

wherein $R^{iv}$, $R_1'''$, $R_4$, $R_5'$ and h are as defined hereinbefore.

The compounds containing methyl groups can be reacted with the anils in the presence of a suitable stongly polar, neutral to alkaline organic solvent which does not contain atoms, in particular hydrogen atoms, that can be replaced by alkali metals. In practice, suitable solvents of this kind are primarily dialkylamides of formic acid and phosphoric acid as well as tetraalkylureas, wherein "alkyl" represents a lower alkyl group of 1 to 4 carbon atoms, in particular a methyl group. As important examples of such solvents there may be mentioned diethyl formamide, hexamethylphosphoric triamide, tetramethylurea, and especially dimethyl formamide. Solvent mixtures are also suitable.

As has been mentioned already, a strongly basic alkali compound is also necessary for carrying out the reaction. Suitable for this purpose, depending on the nature of the solvent and the reactivity of the anil, are specific sodium alcoholates, such as sodium tert.-butylate, and in particular potassium compounds of the composition $KOC_{m-1}H_{2m-1}$, wherein m is an integer from 1 to 6, preferably 2 to 6, for example potassium hydroxide, or especially potassium tert.butylate. When using such alkali alcoholates the process must be carried out in virtually anhydrous medium, whereas a small water content of up to app. 15% (e.g. water of crystallisation) is permissable when using potassium hydroxide. It is advantageous on occasion to use potassium hydroxide or sodium tert.-butylate, in combination with hexamethylphosphoric triamide at elevated temperature, e.g. at 100°-130° C. It will be readily understood that mixtures of such bases can also be used for carrying out the process.

The compounds containing methyl groups are reacted with the anils in equivalent amounts, i.e. in the molar ratio of 1:2, so that there is no substantial excess of either component. An excess of anil of up to approx. 50% is however usually advantageous. It is advantageous to use at least the equivalent amount of alkali compound, i.e. at least 1 mole of a compound with for example, one KO group to 1 mole of aldehyde anil. When using potassium hydroxide, it is preferable to do so in 4 to 8 times the equivalent amount. Particularly good yields are obtained on using potassium tert.butylate in one to six times, preferably two to four times, the equivalent amount.

The reaction according to the invention can usually be carried out at temperatures in the range between about 10° and 150° C. When using particularly reactive anils, the reaction takes place even at room temperature, in which case it is not necessary to apply heat externally. This is advantageous if the reactants contain ring compounds or substituents which can be easily opened or split off by alkali or which can be chemically changed in some other way. This applies, for example, to anils which contain chlorine substituents which can be easily split off. However, it most advantageous to carry out the process at elevated temperature. For example, the reaction mixture is heated slowly to 30° to 80° C. and then kept at this temperature for a time, e.g. from ½ hour to 2 hours.

The manufacture of the anil and the reaction thereof with the tolyl compound can also be carried out consecutively in the one reaction vessel. For example, the aldehyde is heated with excess aniline in dimethyl formamide and the reaction mixture is completely evaporated to dryness in vacuo. The tolyl component and dimethyl formamide are added and the usual procedure is carried out.

The final products can be worked up from the reaction mixture by conventional methods which are known per se. The isolation is effected for example by precipitation with water, whilst water-soluble products are salted out, for example with NaCl, KCl or by neutralisation, if appropriate by acidification with a strong mineral acid, for example hydrochloric acid. In these last mentioned cases, the free sulphonic acids can be precipitated and can, if appropriate, be converted into the corresponding alkali metal, alkaline earth metal, ammonium or amine salts by reaction with alkali salts or alkaline earth salts or with ammonium hydroxide or amines.

The starting materials for obtaining the compounds of the formulae (1), (2), (5), (6), (10), (13), (16) and (23) are known or can be prepared by methods analogous to known ones.

Compounds of the formula (1), wherein n is 1 or 2, and of the formulae (2), (5), (6), (10), (13), (16) and (23), can also be obtained by converting stilbene compounds prepared by methods known per se and which are substituted in the 4,4'-position by amino, cyano and/or modified carboxyl groups, to give the corresponding triazolyl-, 1,2,4-oxdiazolyl-, 1,3,4-oxdiazolyl- or oxazolyl-substituted stilbene compounds in known manner.

4-(v-Triazolyl)-styryl compounds of the formula (1) can also be obtained by reacting a 4-N-oxido-v-triazol-2-yl-benzaldehyde with a compound of the formula (18) and reducing the resultant product by methods which are known per se.

The novel compounds defined above exhibit a more or less pronounced fluorescence in the dissolved or finely divided state. They can be used for optically brightening a wide variety of synthetic, regenerated man-made or natural organic materials or substances which contain such organic materials.

Without any restriction being implied by the following classification, examples of organic materials which can be optically brightened are:

I. Synthetic organic materials of high molecular weight:

(a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on $\alpha,\beta$-unsaturated carboxylic acids or derivatives of such carboxylic acids, especially on acrylic compound for example acrylic esters, acrylic acid, acrylonitrile, acrylic amides and their derivatives or their methacrylic analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals, (c) polycondensation products or precondensates based on bifunctional or polyfunctional compounds with condensable groups, their homocondensation and co-condensation products, and aftertreatment products, for example polyesters, especially saturated polyesters (for example ethylene glycol terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and analogues, polycarbonates and silicones;

(d) polyaddition products, such as polyurethanes (crosslinked and uncrosslinked) and expoxide resins.

II. Regenerated man-made organic materials, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensional structures such as sheets, profiles, injection mouldings, various machined articles, chips, granules or foams, and also predominantly two-dimensional structures, such as films, foils lacquers, coatings and impregnations, or predominantly one-dimensional bodies, such as filaments, fibres, flocks and wires. The said materials can, on the other hand, also be in an unshaped state, in the most diverse homogeneous or inhomogeneous forms of division, as for example, in the form of powders, solutions, emulsions, dispersions, latices, pastes or waxes.

Fibrous materials can, for example, be in the form of endless filaments (stretched or unstretched), staple fibres, flocks, hanks, textile filament yarns, threads, non-wovens, felts, waddings, flocked structures or woven textile or bonded textile farbrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely divided form (suspensions, so-called microdispersions, or optionally solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperatures of 20° to 140° C., for example at the boiling point of the bath or near it (about 90° C.). Solutions or emulsions in organic solvents can also be used for the finishing according to the invention of textile substrates, as is practised in the dyeing industry in so-called solvent dyeing (pad-thermofixation application, or exhaustion dyeing processes in dyeing machines).

The new fluorescent brighteners of the present invention can further be added to, or incorporated in, the materials before or during their shaping. Thus they can for example be added to the compression moulding composition or injection moulding composition during the manufacture of films, sheets (for example incorporated in polyvinyl chloride in a roller mill at elevated temperature) or mouldings.

If the fashioning of man-made synthetic or regenerated man-made organic materials is effected by spinning processes or from spinning solutions/melts, the fluorescent brighteners can be applied by the following processes:

addition to the starting substances (for example monomers) or intermediates (for example precondensates or prepolymers), that is to say before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions, and application to the spun tow before stretching.

The fluorescent brighteners of the present invention can, for example, also be employed in the following use forms:

(a) in mixtures with dyestuffs (shading) or pigments (coloured pigments or especially, for example, white pigments), or as an additive to dye baths, printing pastes, discharge pastes or reserve pastes, or for the aftertreatment of dyeings, prints or discharge prints;

(b) in mixtures with carriers, wetting agents, plasticisers, swelling agents, anti-oxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft handle finishes, antisoiling finishes or anti-static finishes, or antimicrobial finishes;

(d) incorporation of the fluorescent brighteners into polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;

(e) as additives to master batches;

(f) as additives to a wide variety of industrial products in order to render these more marketable (for example improving the aspect of soaps, detergents, pigments);

(g) in combination with other optically brightening substances;

(h) in spinning bath preparations, that is to say as additives to spinning baths which are used for improving the slip for the further processing of synthetic fibres, or from a special bath before the stretching of the fibre;

(i) as scintillators for various purposes of a photographic nature, for example for electrophotographic reproduction or supersensitising;

(j) depending on the substitution as laser dyes.

If the brightening process is combined with textile treatment or finishing methods, the combined treatment can in many cases advatageously be carried out with the aid of appropriate stable preparations which contain the fluorescent brightener compounds in such a concentration that the desired brightening effect is achieved.

In certain cases, the fluorescent brighteners are made fully effective by an after-treatment. This can be, for example, a chemical treatment (for example acid treatment), a thermal treatment (for example heat) or a combined chemical/thermal treatment. Thus, for example, the appropriate procedure to follow in brightening a number of fibre substrates, for example polyester fibres, with the fluorescent brighteners according to the invention, is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperature between 120° and 225° C., for example by heating in a drying chamber, by ironing within the specified temperature range or by treatment with dry, superheated steam. The drying and dry heat treatment can also be carried out in immediate succession or be combined in a single process stage.

The amount of fluorescent brightener of the present invention to be used, referred to the weight of the material to be brightened, can vary within wide limits. A marked and lasting effect can be obtained even with very insignificant amounts, in certain cases 0.0001 percent by weight. But it is also possible to use amounts of up to app. 0.8 percent by weight and, on occasion, up to app. 2 percent by weight. For most practical purposes, it is preferable to use amounts between 0.0005 and 0.5 percent by weight.

For various reasons it is often advantageous not to use the fluorescent brighteners by themselves, i.e. pure, but in admixture with a wide variety of assistants and extenders, for example anhydrous sodium sulphate, sodium sulphate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The fluorescent brighteners of this invention are also particularly suitable for use as additives to wash liquors or heavy duty and domestic detergents, to which they can be added in various ways. They are appropriately added to wash liquors in the form of their solutions in water or organic solvents or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistants, as a dry brightening powder. For example, the brightening agents can be mixed, kneaded or ground with the active detergents and, in this form, admixed with the finished powder. However, they can also be sprayed in a dissolved or pre-dispersed form on the finished detergent.

Suitable detergents are the known mixtures of active detergents, for example soap in the form of chips and powders, synthetics, soluble salts of sulphonic acid hemiesters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerol sulphonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The detergents can further contain for example: antistatic agents, fat restorative skin protectives, such as lanolin, enzymes, anti-microbial agents, perfumes and colourants.

The new fluorescent brighteners have the particular advantage that they are also active in the presence of active chlorine donors, for example, hypochlorite, and can be used without significant loss of effect in wash liquors containing non-ionic washing agents, for example alkylphenolpolyglycol ethers.

The compounds according to the invention are added in amounts of 0.005 to 1% or more, based on the weight of the liquid or pulverulent finished detergent. Wash liquors which contain the indicated amounts of the claimed fluorescent brighteners impart a brilliant appearance in daylight when used to wash textiles made from cellulose fibres, polyamide fibres, cellulose fibres with a high quality finish, polyester fibres or wool.

The washing treatment is carried out as follows, for example:

The textiles are treated for 1 to 30 minutes at 20° to 100° C. in a wash liquor which contains 1 to 10 g/kg of a built-up composite detergent and 0.05 to 1%, based on the weight of the detergent, of the claimed brightening agents. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching additive.

Compounds of the formula (1), wherein $R_2$ and/or $R_3$ represent sulpho, are particularly suitable for brightening cotton and polyamides.

In the following examples, parts and percentages are always by weight, unless otherwise stated. Unless indicated to the contrary, melting points and boiling points are uncorrected.

EXAMPLE 1

6.1 g of 4-(4-methoxy-2H-1,2,3-triazol-2-yl)-benzaldehyde and 10.8 g of 4-(benzoxazol-2-yl)-benzyl-diethyl phosphonate are dissolved in 80 ml of dimethyl formamide at room temperature. Then 3.6 g of sodium methylate are added in portions over the course of 10 minutes and the temperature rises to approx. 38° C. After the exothermic reaction has subsided, the reaction mixture is subsequently stirred for 1½ hours at 40° to 45° C., diluted with 160 ml of methanol and 80 ml of water at a temperature of 15°-20° C. after cooling, and adjusted to a pH of 5 by the dropwise addition of 50% acetic acid. After 1 hour the beige-yellow product is collected with suction, washed with 50% ethanol and dried. Two crystallisations from chlorobenzene with the aid of fuller's earth yields 7.15 g of the compound of the formula

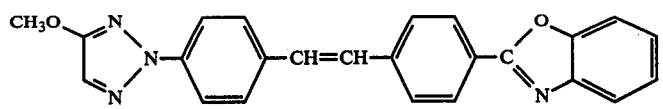

(101)

in the form of slightly yellowish crystal flakes with a melting point of 200°-202° C.

Repetition of the above procedure using an equivalent amount of 4-(2-phenyl-1,3,4-oxdiazol-5-yl)-benzyl-diethyl phosphonate instead of 4-(benzoxazol-2-yl)-benzyl-diethyl phosphonate yields the compound of the formula

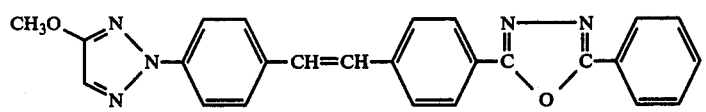

(102)

(crystallisation from chlorobenzene) in the form of fine light yellow crystals with a melting point of 254°-256° C.

The 4-(4-methoxy-2H-1,2,3-triazol-2-yl)-benzaldehyde used as starting material was obtained as follows:

With efficient stirring, 71.5 g of 2-p-tolyl-4-hydroxy-2H-1,2,3-triazole (m.p. 178°-180° C., prepared in accordance with Synthesis 1974 (March), pp. 198-199) are added at room temperature to a mixture of 350 ml of water and 25 g of sodium hydroxide. After half an hour, 64 g of dimethyl sulphate are added dropwise to the reaction mixture over a period of half an hour, in the course of which time the reaction temperature rises to approx. 40° C. and a slighly brownish coloured emulsion forms. After the exothermic reaction has subsided, the mixture is heated for 1 hour to 50°-55° C., then 10 g of calcined sodium carbonate are added and the methylation product is expelled with steam. To the distillate is added 10% sodium chloride and the oily product is taken up in methylene chloride, dried over magnesium sulphate and the solvent is distilled off after filtration. Distillation in vacuo yields 50 g of 2-p-tolyl-4-methoxy-2H-1,2,3-triazole (b.p. 145°-149° C.) as a slightly yellowish liquid.

44.4 g of 2-p-tolyl-4-methoxy-2H-1,2,3-triazole are mixed with 400 ml of dry carbon tetrachloride. After addition of 47 g of N-bromosuccinimide and 0.25 g of dibenzoyl peroxide, the mixture is boiled at reflux and irradiated with UV-light for 2 minutes. After a reaction time of 2 hours, the batch is allowed to cool, succinimide is removed by filtration and the solvent is evaporated completely at elevated temperature in vacuo. The residue consists of 65 g of crude 2-(4-bromo-methylphenyl)-4-methoxy-2H-1,2,3-triazole in the form of a light brown oil which crystallises rapidly. A sample for analysis which is recrystallised from isopropanol gives colourless crystals with a melting point of 65°-67° C.

With stirring, 18.2 g of crude bromomethyl compound are added to a solution of 18.3 g of hexamethylenetetramine in 150 ml of chloroform and after a few minutes, with formation of latent heat, the addition compound falls out in crystalline form. The slurry is refluxed for 1 hour, cooled, and the solid is collected with suction, washed with chloroform and dried to yield 22.1 g of crude addition compound with a melting point of 178°-179° C. (with decomp.). Thereafter 21.8 g of the addition compound are stirred with 110 ml of 50% acetic acid for 2¾ hours at 90°-95° C. After cooling, the crystalline solid is separated, washed with 50% acetic acid and then dried at 30°-40° C. in vacuo to yield 7.6 g of virtually pure 4-(4-methoxy-2H-1,2,3-triazol-2-yl)-benzaldeyde. Crude melting point: 103°-104° C. A sample for analysis crystallised from isopropanol gives colourless crystals. Melting point: 105°-106° C.

EXAMPLE 2

A mixture of 5.9 g of 2,5-dimethyl-benzoxazole, 8.95 g of 4-(4-methoxy-2H-1,2,3-triazol-2-yl)-benzaldehyde, 8.75 g of p-toluenesulphonic acid, 4 ml of dimethyl formamide and 80 ml of xylene is heated to the boil for 8 hours with stirring at reflux, during which time the water of reaction which forms is continuously distilled off with the aid of a steam trap. After the reaction mixture has cooled, the solid is collected with suction, covered first with 95% alcohol and then with 2% sodium carbonate solution and thereafter with water and dried. One crystallisation from chlorobenzene with fuller's earth and a subsequent crystallisation from isopropanol gives 5.3 g of the compound of the formula

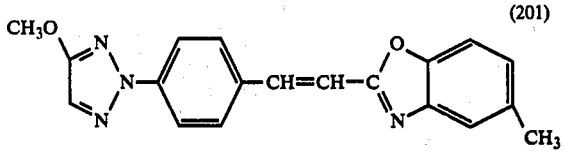

(201)

17 in the form of slighly yellowish crystals with a melting point of 175°–177° C.

EXAMPLE 3

10.35 g of 4-(4-methoxy-5-chloro-2H-1,2,3-triazol-2-yl)-2-chlorobenzyldiethyl phosphonate and 5.62 g of 4-(5-phenyl-1,3,4-oxdiazol-2-yl)-benzaldehyde are dissolved with slight warming in 80 ml of dimethyl formamide. After the solution has cooled to 25° C., 2.8 g of sodium methylate are added in portions over a period of 10 minutes while the temperature is kept at a maximum of 35° C. by cooling from time to time. The reaction mixture is thereafter heated to 40° C., then cooled to 15° C., diluted with 75 ml of methanol and 100 ml of water and adjusted to a pH of 5–6 by adding 50% acetic acid. The yellow solid is separated, washed with 50% ethanol and dried. Two crystallisations from chlorobenzene with fuller's earth yield 5.7 g of the compound of the formula

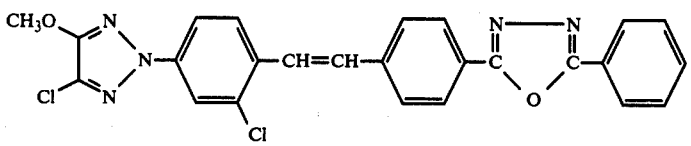

(301)

in the form of light yellow crystals with a melting point of 247°–249° C. Repetition of the above described procedure using an equivalent amount of 4-(benzoxazol-2-yl)-benzaldehyde yields a compound of the formula

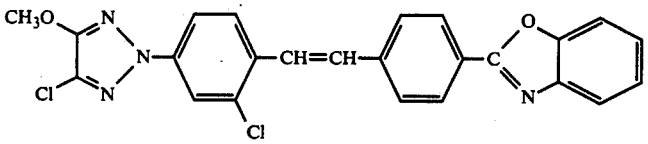

(302)

(crystallisation from chlorobenzene) in the form of fine, felted, light yellow needles with a melting point of 250°–251.5° C.

The phosphonate used as starting material was prepared as follows:

113 g of 2-(3-chloro-4-methylphenyl)-4-hydroxy-2H-1,2,3-triazole-1-oxide (m.p. 166°–170° with decomp., prepared in accordance with Synthesis 1974 (March), pp. 189–199) are added at room temperature to a solution of 43 g of 85% potassium hydroxide in 750 ml of water. With efficient stirring, 79 g of dimethyl sulphate and simultaneously 55 ml of 30% potassium hydroxide solution are added to the reaction mixture in the course of 15 minutes while maintaining an internal temperature of 25°–35° C. by cooling. The batch is subsequently heated for 1 hour to 45°–50° C., and cooled to room temperature. The solid is then collected with suction, washed with water and dried. One crystallisation from isopropanol yields 30 g of 2-(3-chloro-4-methylphenyl)-4-methoxy-2H-1,2,3-triazole-1-oxide in the form of colourless crystals. Melting point: 106°–108° C.

18

24 g of the above oxide compound are added to a mixture of 150 ml of dioxan and 157 ml of 37.2% hydrochloric acid and the batch is heated to the boil of reflux with stirring while introducing a moderate flow of gaseous hydrochloric acid. After a reaction time of 2 hours, the reaction mixture is evaporated to dryness by rotary evaporation. One crystallisation of the residue from isopropanol yields 21.5 g of 2-(3-chloro-4-methoylphenyl)-4-methoxy-5-chloro-2H-1,2,3-triazole in light beige-coloured crystals. Melting point: 85°–87° C.

20.8 g of the above triazole compound are brominated with 16.3 g of N-bromosuccinimide and 0.1 g of dibenzoyl peroxide in carbon tetrachloride while irradiating briefly with UV-light. Working up and crystallisation from isopropanol yields 17 g of 2-(3-chloro-4-bromomethylphenyl)-4-methoxy-5-chloro-2H-1,2,3-triazole in the form of colourless crystals. Melting point: 141°–142° C.

16.85 g of the above bromomethyl compound are heated with 10 ml of triethyl phosphite in the course of 1½ hours to 140°–150° C. while distilling off ethyl bromide. The batch is kept for 1½ hours at the same temperature and then excess triethyl phosphite is completely evaporated at 100° C. bath temperature and 10 mm mercury column to yield 20.7 g of crude phosphonate as a viscous oil which is used as such for condensation.

EXAMPLE 4

9.5 of 5-(4-methoxy-2H-1,2,3-triazol-2-yl)-2-chlorobenzyl-diethyl phosphonate and 5.34 g of 4-(4-methoxy-2H-1,2,3-triazol-2-yl)-2-chlorobenzaldehyde are dissolved by heating in 50 ml of dimethyl formamide and the solution is then cooled to 25° C. Then 2.8 g of sodium methylate are added in portions and the reaction mixture is stirred for 1½ hours at 40°–45° C. and worked up as described in Example 1. Two crystallisations from toluene with fuller's earth yield 5.9 g of the compound of the formula

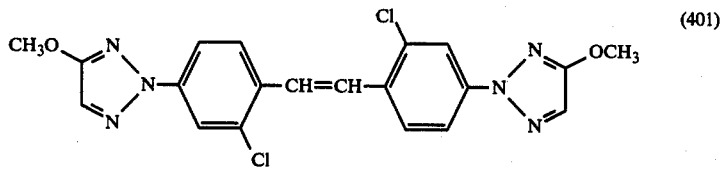

(401)

in the form of light yellow needles with a melting point of 225°–226° C. The aldehyde was prepared from 2-(3-chloro-4-methylphenyl)-4-hydroxy-2H-1,2,3-triazole (m.p. 207°–108° C.) as described in Example 1 and has a melting point of 118°–119° C.

The phosphonate was prepared from 2-(3-chloro-4-bromomethylphenyl)-4-methoxy-2H-1,2,3-triazole (m.p. 87°–89° C., intermediate stage of the above aldehyde) and triethyl phosphite in the customary manner. It is a colourless viscous oil which crystallises slowly.

Repetition of the above described procedure using as phosphonate component an equivalent amount of 4-(benzoxazol-2-yl)- or 4-(5-phenyl-1,3,4-oxdiazol-2-yl)-benzyl-diethyl phosphonate yields the compound of the formula

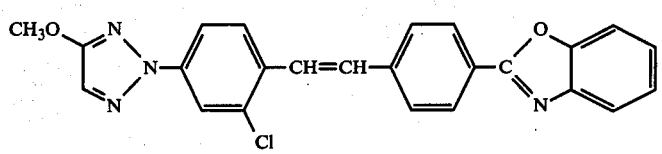

(crystallisation from toluene) in the form of slightly greenish-yellow crystals with a melting point of 217°–217.5° C., or of the formula

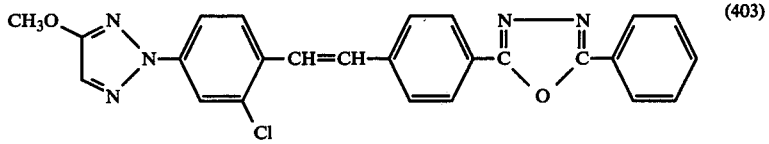

(crystallisation from chlorobenzene) in the form of fine crystals with a melting point of 224°–226° C.

EXAMPLE 5

2.23 g (0.01 mole) of 2-(p-tolyl)-6-methyl-benzoxazole of the formula

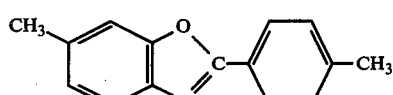

and 3.13 g (0.01 mole) of the Schiff's base obtained from 2-(p-formylphenyl)-4-methoxy-2H-1,2,3-triazole and o-chloroaniline of the formula

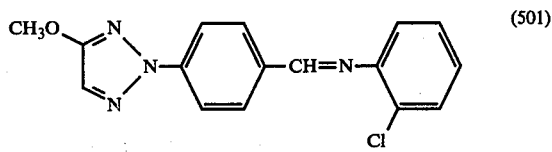

and 2.5 g of potassium hydroxide powder with a water content of approx. 15% are stirred in 50 ml of dimethyl formamide for 1 hour at 22° to 29° C. under nitrogen. During the first 10 minutes of the reaction, the reaction mixture is irradiated with UV-light with a wavelength of over 300 nm. Then 250 ml of methanol are added to the violet suspension and the batch is cooled to approx. −10° C. The precipitated product is collected with suction, washed with methanol and dried in vacuo at 50° to 60° C. to yield 3.5 g (85.6% of theory) of the product of the formula

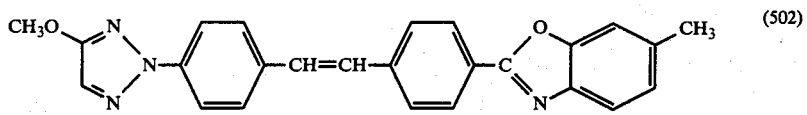

Two recrystallisations from two 130 ml portions of toluene with fuller's earth yield 2.85 g (69.72% of theory) of light yellow greenish crystals with a melting point of 189°–190° C.

The compounds of the formula

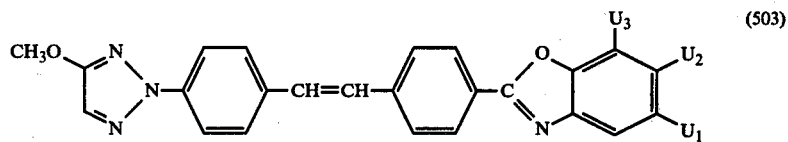

listed in Table 1 are prepared in analogous fashion.

TABLE 1

| No. | $U_1$ | $U_2$ | $U_3$ | Melting point |
|-----|-------|-------|-------|---------------|
| 504 | —C(CH$_3$)$_3$ | —H | —H | 203 – 204° C |
| 505 | —CH$_3$ | —H | —CH$_3$ | 188 – 187° C |
| 506 | —CH$_3$ | —CH$_3$ | —H | 233 – 234° C |
| 507 | —OCH$_3$ | —H | —H | 183 – 184° C |
| 508 | —H | —C$_6$H$_5$ | —H | 245 – 247° C |
| 509 | —CH$_3$ | —H | —H | 185 – 186° C |
| 510 | —H | —H | —CH$_3$ | 172 – 173° C |
| 511 | —H | —H | —H | 200 – 202° C |

The Schiff's base of the formula (501) was prepared as follows:

20.3 g of 4-(4-methoxy-2H-1,2,3-triazol-2-yl)-benzaldehyde, 12.75 g of o-chloroaniline and 0.2 g of boric acid were refluxed for 3 hours in 50 ml of xylene while the water formed during the reaction was removed by means of a steam trap (1.7 ml of water). The reaction mixture was then cooled to 80° C. and poured into 500 ml of methanol. The light yellow suspension was cooled, the crystallised product collected with suction and dried in vacuo to yield 24.7 g of the compound of the formula (501) with a melting point of 120° C.

EXAMPLE 6

The procedure described in Example 5 is repeated using 2.36 g of 5-(p-tolyl)-3-phenyl-1,2,4-oxdiazole instead of compound (500). Yield: 3.9 g (92.7% of theory) of the compound of the formula

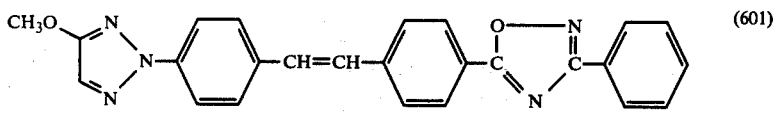

Two recrystallisations from 150 ml portions of toluene with fuller's earth yields 3.4 g (80.8% of theory) of light yellow greenish needles with a melting point of 188°-190° C.

The compounds of the formula

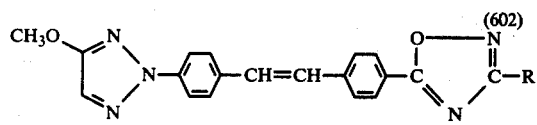

listed in Table 2 are prepared in analogous fashion.

TABLE 2

| No. | R | Melting point |
|---|---|---|
| 603 | —⌬—Cl | 183 – 184° C |
| 604 | —⌬—CH$_3$ | 167 – 168° C |

EXAMPLE 7

The procedure described in Example 5 is repeated using 3.12 g of 5-(p-tolyl)-2-biphenyl-1,3,4-oxdiazole instead of compound (500) to yield after two recrystallisations of the crude product from toluene with fuller's earth the compound of the formula

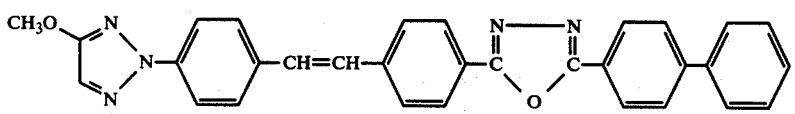

in the form of white lamellae which melt at 240°-242° C.

EXAMPLE 8

2.37 g (0.01 mole) of 2-(p-tolyl)-5,7-dimethyl-benzoxazole of the formula

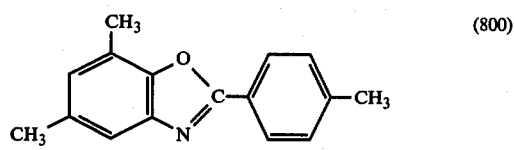

and 3.47 g (0.01 mole) of the Schiff's base obtained from 2-(p-formylphenyl)-4-methoxy-5-chloro-2H-1,2,3-triazole and p-chloroaniline of the formula (801)

and 2.5 g of potassium hydroxide powder (content 90%) are stirred in 100 ml of dimethyl formamide for 1 hour at 22° to 30° C. under nitrogen. During the first 10 minutes of the reaction, the reaction mixture is irradiated with UV-light having a wavelength of over 300 nm. Then 400 ml of methanol are added to the violet suspension and the bath is cooled to approx. −10° C. The precipitated product is collected with suction, washed with methanol and dried in vacuo at 50°-60° C.

Yield: 2.7 g (59.1% of theory) of the product of the formula

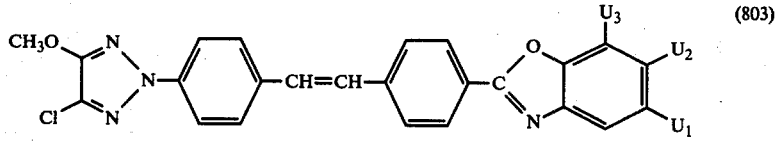

One crystallisation from 80 ml of toluene with fuller's earth yields 1.8 g (39.4% of theory) of light yellow greenish crystals with a melting point of 216.5°-217.5° C.

The compounds of the formula (803)

listed in Table 3 are prepared in analogous fashion.

TABLE 3

| No. | U₁ | U₂ | U₃ | Melting point |
|-----|-----|-----|-----|---------------|
| 804 | -C(CH₃)₃ | -H | -H | 212 – 213° C |
| 805 | -CH₃ | -CH₃ | -H | 301 – 302° C |
| 806 | -H | -CH₃ | -H | 285 – 288° C |
| 807 | -OCH₃ | -H | -H | 310 – 311° C |
| 808 | CH₃ | -H | -H | 300 – 308° C (decomposition) |
| 809 | -H | -H | -CH₃ | 244 – 245° C |

The Schiff's base of the formula (801) was prepared as follows:

23.75 g (0.1 mole) of 4-(4-methoxy-5-chloro-2H-1,2,3-triazol-2-yl)-benzaldehyde, 12.75 g of p-chloroaniline and 0.2 g of boric acid were refluxed for 3 hours in 50 ml of xylene while the water formed during the reaction was removed by means of a steam trap (1.1 ml). The reaction mixture was then cooled to 80° C. and poured into 500 ml of methanol. The light yellow suspension was cooled and the crystallised product collected with suction, washed and dried in vacuo. Yield: 32.5 g (93.7% of theory) of the compound of the formula (801) with a melting point of 150° C.

The aldehyde used as starting material was prepared as follows:

81.4 g of 2-(p-tolyl)-4-hydroxy-2H-1,2,3-triazole-1-oxide (m.p. 150°-154° C. with decomp., prepared in accordance with Synthesis 1974 (March), pp. 198-199) are dissolved in 810 ml of dimethyl formamide at room temperature. Then 141.3 g of potassium carbonate are suspended in this solution and 48.3 ml of methyl iodide are poured into the suspension with good stirring. The batch is then heated to 60° C. over 30 minutes and kept thereat for 6 hours. The fine suspension is thereafter poured into 6 liters of water, and the pH is adjusted to 4–5 with 2N sulphuric acid. After cooling to room temperature, the solid is collected with suction, washed with water and dried to yield 56.5 g of 2-(p-tolyl)-4-methoxy-2H-1,2,3-triazole-1-oxide with a melting point of 62°-64° C. After recrystallisation from alcohol/water the product melts at 70°-72° C.

80.4 g of 2-p-tolyl)-4-methoxy-2H-1,2,3-triazole-1-oxide are dissolved in 531 ml of dioxan and, with good stirring, a moderate flow of gaseous hydrochloric acid is introduced over approx. 2 hours while the temperature rises gradually to approx. 61° C. Thereafter the reaction mixture is heated in the course of 30 minutes to boiling temperature and stirred for approx. 1½ hours at this temperature. After it has cooled to room temperature, the batch is poured with stirring into 2.7 liters of water and the precipitated solid is collected with suction and dried to yield 82.9 g of 2-(p-tolyl)-4-methoxy-5-chloro-2H-1,2,3-triazole with a melting point of 59° to 62° C. After recrystallisation from isopropanol, the product melts at 72°-73° C.

82.9 g of 2-(p-tolyl)-4-methoxy-5-chloro-2H-1,2,3-triazole are brominated with 74.2 g of N-bromosuccinamide and 0.37 g of dibenzoyl peroxide in carbon tetrachloride as in Example 1 and worked up. Yield: 58.9 g of 2-(p-bromomethylphenyl)-4-methoxy-5-nitro-2H-1,2,3-triazole with a melting point of 110°-116° C. After recrystallisation from isopropanol the melting point is 121°-122° C.

58.9 g of bromomethyl compound are reacted with 54.1 g of hexamethylenetetramine in 920 ml of chloroform at boiling temperature as in Example 1. Working up yields almost white crystals with a melting point of 158°-161° C. (with decomp.). This compound is refluxed in 400 ml of 50% acetic acid for 3 hours. After cooling to room temperature, the solid is collected with suction, washed with water and dried to yield 29.4 g of 2-(p-formyl-phenyl)-4-methoxy-5-chloro-2H-1,2,3-triazole in the form of white crystals with a melting point of 138°-140° C. After recrystallisation from isopropanol the melting point is 147°-148° C.

EXAMPLE 9

Using softened water, a bath is prepared which contains, per liter, 0.16% (referred to the weight of the fabric to be brightened) of the compound of the formula (101) or (201) (which has been predispersed with a small amount of water and app. 1 gram of a dispersant, e.g. an ethoxylated stearyl alcohol) and approx. 2 g of a carrier. A suitable carrier is, for example, a mixture of dodecylbenzenesulphonate (as triethanolamine salt), ethoxylated ricinolic acid, n-hexanol and ethylene glycol in 1,2,4-trichlorobenzene.

A polyester fabric is put into this bath at 40° C. (liquor ratio 1:25). The bath is heated to 97° C. in the course of 30 minutes and held at this temperature for a further 30 minutes. After rinsing and drying, a very strongly brightened polyester fabric is obtained.

EXAMPLE 10

A cellulose acetate fabric is put at 50° C. into an aqueous bath (liquor ratio 1:30 to 1:40) which contains 0.15% (based on the weight of the fabric) of the compound of the formula (101). The temperature of the treatment bath is brought to 90°-95° C. and kept thereat for 30 to 45 minutes. After the fabric has been rinsed and dried, a good white effect is obtained.

EXAMPLE 11

A polyamide fabric (Perlon) is put at 60° C., in the liquor ratio of 1:40, into a bath which contains (referred to the weight of the fabric) 0.1% of a fluorescent brightener of the formula (101), (102) or (402) and, per liter, 1 g of 80% acetic acid and 0.25 g of an adduct of 30 to 35 moles of ethylene oxide and 1 mole of commercial stearyl alcohol. The bath is heated within 30 minutes to boiling temperature and kept at the boil for 30 minutes. The fabric is then rinsed and dried. A strong white effect of good light fastness is obtained.

Similar white effects are obtained by using a fabric made of polyamide 66 (nylon) instead of polyamide 6.

Finally, it is also to carry out the process under high temperature conditions, e.g. over the course of 30 minutes at 130° C. For this kind of application it is advisable to add 3 g/l of hydrosulphite to the solution.

EXAMPLE 12

Polypropylene fibres are treated with 0.02 to 0.4% of the formula (101) for 60 minutes at 60° to 100° C. in a bath (liquor ratio 1:40) which contains, per liter, 5 g of an adduct of approx. 35 moles of ethylene oxide and 1 mole of octadecyl alcohol, and 0.5 g of trisodium phosphate. The material is then rinsed and dried. The polypropylene fibres have a markedly higher white content than untreated fibres.

A similar effect is obtained by using 1 g of 85% formic acid instead of 0.5 g of trisodium phosphate.

EXAMPLE 13

A polyester fabric (e.g. "Dacron") is padded at room temperature with an aqueous dispersion which contains, per liter, 2 g of a compound of the formula (101), (102), (201), (401) or (402) as well as 1 g of an adduct of approx. 8 moles of ethylene oxide and 1 mole of p.tert.-octylphenol, and dried at approx. 100° C. The dry material is subsequently subjected to a heat treatment at 150° to 220° C., which lasts from 2 minutes to a few seconds, depending on the temperature. The treated material has a markedly whiter appearance than untreated material.

EXAMPLE 14

A modified polyester fabric (Dacron 64 ®) prepared from co-condensation of 2 to 5 molar percent of isophthalic acid-5-sodium sulphonate is padded to a liquor pick-up of 70% with a liquor containing, per liter, 2.5 g of the compound of the formula (101), (102), (201), (401) or (402) and 0.1 g of an adduct of 2 to 5 moles of ethylene oxide and 1 mole of polyphenol. The fabric is dried for 20 minutes at 70° C. The dry fabric is subsequently thermofixed for 30 seconds at 220° C., washed for 30 minutes at 97° C. at a liquor ratio of 1:30 in a wash liquor which contains, per liter, 5 g of soap and 2 g of sodium carbonate, rinsed in running cold water and finally dried with a hot iron at 180° C.

The treated fabric has a markedly whiter appearance than untreated fabric.

EXAMPLE 15

100 Parts of granulated terephthalic acid/ethylene glycol-polyester are homogeneously mixed with 0.05 part of one of the compounds of the formulae (101) or (102) in a roller vessel. With stirring, the mixture is fused at 285° C. and spun through spinnerets. Strongly whitened polyester fibres are obtained. The above compound can also be added before or during the polycondensation to give the polyester.

EXAMPLE 16

A homogeneous mixture of 100 parts of polyvinyl chloride, 3 parts of stabiliser (Advastat BD 100: Ba/Cd complex), 2 parts of titanium dioxide, 59 parts of dioctyl phthalate, and 0.01 to 0.2 part of one of the compounds of the formula (101), (102) or (201), are rolled out to a sheet on a calender at 150° C. to 155° C.

The so obtained opaque polyvinyl chloride sheet possesses a substantially higher white content than a sheet which does not contain the fluorescent brightener.

EXAMPLE 17

A casting composition which consists of 10 g of polyacrylonitrile, 0.2 g of titanium dioxide (anatase modification) as matting agent, and 40 ml of dimethyl formamide, and which contains 5 mg of one of the compounds of the formula (101) or (102) is poured onto a glass plate and drawn out with a metal rod to a thin film. After it has dried, the film is strongly whitened.

EXAMPLE 18

A solution of 0.05 to 0.2 part of the compound of the formula (101) in hot acetone or dimethyl formamide is added to a cellulose acetate spinning solution consisting of 100 parts of cellulose acetate (2½-acetate) and 300 parts of acetone, and the well stirred mixture is spun in the conventional manner to filaments.

The resultant filaments have a substantially higher white content than untreated filaments.

EXAMPLE 19

100 Parts of polystyrene and 0.1 part of the compound of the formula (101) are fused, with the exclusion of air, for 20 minutes at 210° C. in a tube measuring 1 cm in diameter. After cooling, an optically brightened polystyrene composition of good lightfastness is obtained.

I claim:

1. 4-(v-Triazolyl)-styryl compounds of the formula

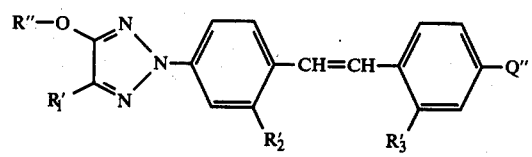

wherein
R" represents alkyl of 1 to 12 carbon atoms which is unsubstituted or substituted by alkoxy, hydroxyl, carboxyl, carbalkoxy or cyano, alkenyl of 3 to 5 carbon atoms or unsubstituted or substituted benzyl,
$R_1'$ represents hydrogen, chlorine, bromine, or the group —$CH_2$—Z, wherein Z represents hydroxyl, benzyloxy, benzyloxy which is substituted by alkyl or alkoxy of 1 to 4 carbon atoms or by halogen, alkanoyloxy of 1 to 4 carbon atoms, alkoxy or alkylmercapto of 1 to 4 carbon atoms, a dialkylamino group containing 1 to 4 carbon atoms in each alkyl moiety, morpholino, piperidino, methyl-substituted morpholino or piperidino, or dialkylphosphono which contains 1 to 4 carbon atoms in each alkyl moiety, each of
$R_2'$ and $R_3'$ independently represents hydrogen, chlorine or cyano, and
Q" represents a benzoxazol-2-yl, 2-aryl-1,3,4-oxdiazol-5-yl or 3(5)-aryl-1,2,4-oxdiazol-5(3)-yl group which is unsubstituted or substituted by non-chromophoric groups.

2. 4-(v-Triazolyl)-styryl compounds according to claim 1 of the formula

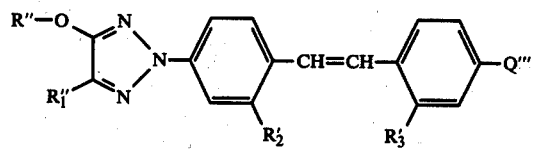

wherein
R" represents alkyl of 1 to 12 carbon atoms which is unsubstituted or substituted by alkoxy, hydroxyl, carboxyl, carbalkoxy or cyano, alkenyl of 3 to 5 carbon atoms or unsubstituted or substituted benzyl,
$R_1''$ represents hydrogen, chlorine or the group —$CH_2$—Z', wherein Z' represents hydroxyl, benzyloxy, alkanoyloxy of 1 to 4 carbon atoms, or alkoxy of 1 to 4 carbon atoms, each of
$R_2'$ and $R_3'$ independently represents hydrogen, chlorine or cyano, and
Q''' represents a radical of the formula

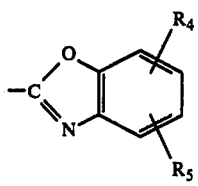

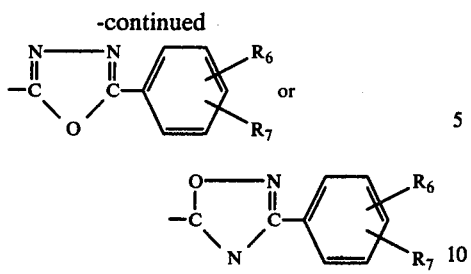

wherein
R₄ represents hydrogen or alkyl of 1 to 4 carbon atoms,
R₅ represents hydrogen, chlorine, alkyl of 1 to 4 carbon atoms, alkoxy of 1 to 4 carbon atoms, alkylsulphonyl of 1 to 4 carbon atoms, phenyl, phenylalkyl containing 1 to 4 carbon atoms in the alkyl moiety, cyclohexyl, carboxyl, carbalkoxy containing 1 to 4 carbon atoms in the alkoxy moiety or phenylsulphonyl,
R₆ represents hydrogen, alkyl of 1 to 4 carbon atoms, alkoxy of 1 to 4 carbon atoms, chlorine, phenyl, phenylalkyl containing 1 to 4 carbon atoms in the alkyl moiety, or together with R₇ completes a fused benzene ring,
R₇ represents hydrogen, alkyl of 1 to 4 carbon atoms, alkoxy of 1 to 4 carbon atoms, or together with R₆ completes a fused benzene ring.

3. 4-(v-Triazolyl)-styryl compounds according to claim 2 of the formula

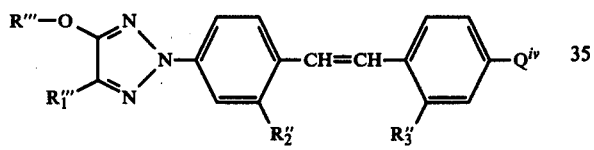

wherein
R''' represents alkyl of 1 to 4 carbon atoms, allyl or benzyl,
R₁''' represents hydrogen or chlorine, each of
R₂'' and R₃'' independently represents hydrogen or chlorine, and
Q''' represents a radical of the formula

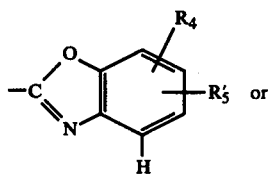

wherein
R₄ represents hydrogen or alkyl of 1 to 4 carbon atoms,
R₅' represents hydrogen, chlorine, alkyl of 1 to 4 carbon atoms, alkylsulphonyl of 1 to 4 carbon atoms or carbalkoxy which contains 1 to 4 carbon atoms in the alkoxy moiety,
R₆' represents hydrogen, alkyl of 1 to 4 carbon atoms, alkoxy of 1 to 4 carbon atoms, chlorine, phenyl, or together with R₇' completes a fused benzene ring, and
R₇' represents hydrogen or together with R₆' completes a fused benzene ring.

4. 4-(v-Triazolyl)-styryl compounds according to claim 3 of the formula

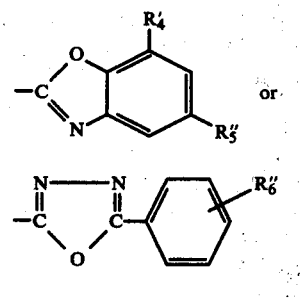

wherein
R'ⁱᵛ represents alkyl of 1 to 4 carbon atoms or benzyl,
R₁''' represents hydrogen or chlorine, each of R₂'' and R₃'' independently represents hydrogen or chlorine, and
Qᵛ represents a radical of the formula

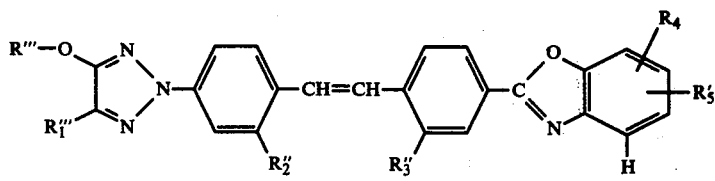

wherein each of
R₄' and R₅'' independently represents hydrogen or methyl and
R₆'' represents hydrogen, chlorine, methyl or methoxy.

5. 4-((v-Triazolyl)-styryl compounds according to claim 3 of the formula

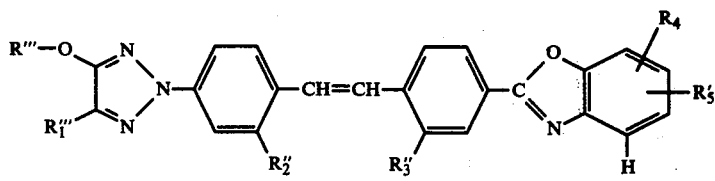

wherein
R''' represents alkyl of 1 to 4 carbon atoms, allyl or benzyl,
R₁''' represents hydrogen or chlorine, each of $R_2''$ and $R_3''$ independently represents hydrogen or chlorine, $R_4$ represents hydrogen or alkyl of 1 to 4 carbon atoms, and $R_5'$ represents hydrogen, chlorine, alkyl of 1 to 4 carbon atoms, alkylsulphonyl of 1 to 4 carbon atoms or carbalkoxy containing 1 to 4 carbon atoms in the alkoxy moiety.

6. A process for optically brightening organic material which comprises incorporating in, or applying to, said material 0.005 to 1% by weight of a 4-(v-triazolyl)-styryl compound as defined in claim 1.

7. A process according to claim 6, wherein the organic material to be optically brightened comprises polyester, polyamide and cellulose acetate.

* * * * *

UNITED STATES PATENT OFFICE
CERTIFICATE OF CORRECTION

Patent No. 4,138,552　　　　　Dated February 6, 1979

Inventor(s) Hans Schlapfer, deceased
Nelly Schlapfer, Legal Representative

It is certified that error appears in the above-identified patent and that said Letters Patent are hereby corrected as shown below:

Claim 2, column 27, line 10, in the left-hand ring of the structure,

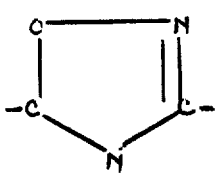　　should be --　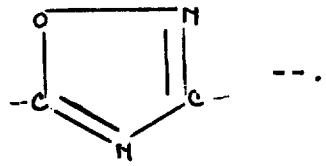　--.

Signed and Sealed this

Nineteenth Day of June 1979

[SEAL]

Attest:

RUTH C. MASON
*Attesting Officer*

DONALD W. BANNER
*Commissioner of Patents and Trademarks*